United States Patent [19]
Mark

[11] Patent Number: 5,653,877
[45] Date of Patent: *Aug. 5, 1997

[54] WATER PURIFICATION SYSTEM HAVING MULTI-PASS ULTRAVIOLET RADIATION AND REVERSE OSMOSIS CHAMBERS

[75] Inventor: Farvell M. Mark, Phoenix, Ariz.

[73] Assignee: FM Mark Electronics Incorporated, Phoenix, Ariz.

[*] Notice: The term of this patent shall not extend beyond the expiration date of Pat. No. 5,451,791.

[21] Appl. No.: 529,623

[22] Filed: Sep. 18, 1995

Related U.S. Application Data

[63] Continuation-in-part of Ser. No. 385,740, Feb. 8, 1995, Pat. No. 5,451,791, which is a continuation of Ser. No. 273,281, Jul. 11, 1994, abandoned, which is a continuation of Ser. No. 987,634, Dec. 9, 1992, abandoned.

[51] Int. Cl.[6] .................................................. C02F 1/48
[52] U.S. Cl. .......................... 210/259; 210/748; 250/435; 250/436; 250/438
[58] Field of Search ................................ 210/259, 748; 258/436, 438, 435

[56] References Cited

U.S. PATENT DOCUMENTS 5,445,729  8/1995  Monroe et al. ................... 210/258
5,451,791  9/1995  Mark ................................. 250/439

*Primary Examiner*—Neil McCarthy
*Attorney, Agent, or Firm*—Harry M. Weiss; Jeffrey D. Moy; Harry M. Weiss & Associates, P.C.

[57] ABSTRACT

A water purification system is disclosed comprising a reverse osmosis chamber coupled to a multi-pass ultraviolet chamber for irradiating water with ultraviolet light radiation both before and after the water passes through the reverse osmosis chamber. The multi-pass ultraviolet chamber provides a plurality of water conveying tubes in proximity to an ultraviolet light radiation source. The diameter of the conveying tubes is substantially larger than the diameter of conduits feeding the tubes. Accordingly, the water flow through the tubes decelerates, thereby increasing the duration of ultraviolet light radiation exposure to the water in the tubes. Additionally, a removable cover is located above the ultraviolet light bulb in order to facilitate easy replacement of the bulb.

11 Claims, 2 Drawing Sheets

WATER PURIFICATION SYSTEM HAVING MULTI-PASS ULTRAVIOLET RADIATION AND REVERSE OSMOSIS CHAMBERS

RELATED APPLICATION

This patent application is a Continuation-In-Part of co-pending patent application entitled "Water Disinfecting Apparatus" under Ser. No. 08/385,740, filed Feb. 8, 1995, U.S. Pat. No. 5,451,791 in the name of the same inventor, and is incorporated herein by reference, which is a Continuation of the patent application Ser. No. 08/273,281, filed Jul. 11, 1994, now abandoned, and which is a Continuation of the patent application Ser. No. 07/987,634 filed Dec. 9, 1992, now abandoned.

BACKGROUND OF THE INVENTION

1. Field of the Invention

This invention is in the field of water purification systems and, more particularly, is a water purification system having a multi-pass ultraviolet radiation chamber and a reverse osmosis chamber.

2. Description of the Related Art

Mechanical and chemical filtration of water for drinking purposes is well known. Mechanical filtration removes sediment and particulate matter of a certain minimal size from water as a function of the filtration elements. Chemical filtration (such as activated charcoal) filters various chemicals that may be present. To kill bacteria, viruses and other microorganisms irradiation with radiant energy from a source of ultraviolet radiation is known. To achieve such kill results, the water is usually passed through a conduit transparent to ultraviolet radiation. The proximity of the source of ultraviolet radiation to such a conduit affects the intensity or concentration of the radiation dosage present. Additionally, the duration of exposure of the water in the conduit to the ultraviolet radiation affects the efficiency of the process in killing bacteria, viruses, and other microorganisms. Therefore, there existed a need to provide an improved water purification system having an ultraviolet light radiation source in close proximity to a plurality of water conveying tubes, and having means for increasing the duration of ultraviolet light radiation exposure to the water in each tube. Additionally, it is advantageous in such an improved system to have a removable cover on the multi-pass ultraviolet light radiation chamber in order to permit a user to quickly and easily replace the ultraviolet light bulb. Lastly, the instant system is further improved by implementing the multi-pass ultraviolet light radiation chamber with a reverse osmosis chamber.

SUMMARY OF THE INVENTION

An object of the present invention is to provide an improved water purification system.

Another object of the present invention is to provide an improved water purification system which exposes fluid to ultraviolet light radiation before the fluid enters a reverse osmosis chamber and after the fluid exits the reverse osmosis chamber.

A further object of the present invention is to provide an improved water purification system which increases the duration of ultraviolet light radiation exposure to fluid conveyed in a tube.

It is further object of the present invention is to provide an improved water purification system having a removable cover from a multi-pass ultraviolet light radiation chamber for permitting easy replacement of an ultraviolet light bulb therein.

Another object of the present invention is to provide an improved water purification system which increases the length of time required before a water storage tank needs cleaning.

BRIEF DESCRIPTION OF THE PREFERRED EMBODIMENTS

According to the present invention, the preferred embodiment of the water purification system is disclosed comprising, in combination, reverse osmosis means for filtering a fluid passing therethrough, multi-pass ultraviolet chamber means coupled to the reverse osmosis means for irradiating the fluid with ultraviolet light radiation both before and after the fluid passes through the reverse osmosis means. The multi-pass ultraviolet chamber means comprises a housing, a pair of support members coupled to opposing inner surface wall portions of the housing, ultraviolet light radiation means coupled between the pair of support members for irradiating the fluid passing through the multi-pass ultraviolet chamber means, first tube means coupled between the pair of support members for conveying the fluid past the ultraviolet light radiation means prior to the fluid entering the reverse osmosis means, second tube means coupled between the pair of support members for conveying the fluid past the ultraviolet light radiation means after the fluid has departed from the reverse osmosis means, and a removable cover located above the ultraviolet light radiation means, the first tube means, and the second tube means. Note that each of the support means have conduit means in fluid communication with the first and the second tube means for conveying the fluid therethrough, and the diameters of the first and the second tube means are substantially larger than the diameters of corresponding conduit means. The system further comprises first filter means coupled to an inlet supply of the fluid for filtering the fluid prior to supplying to the first tube means. An outlet of the first tube means is coupled to an inlet of the reverse osmosis means, and the reverse osmosis means provides a first and second output flow of the fluid. The system further comprises permeate pump means driven by the first output flow of the fluid from the reverse osmosis means for pumping the second output flow of the fluid from the reverse osmosis means. Additionally, the system includes air gap faucet means coupled to the first flow from the permeate pump for conveying the first flow to a drain. An air-loaded storage tank means is coupled to the second flow from the permeate pump for storing the fluid and for supplying the fluid to a header. Second filter means are coupled to the header for filtering the fluid from the permeate pump and from the air-loaded storage tank means. The discharge from the second filter means is coupled to an input of the second tube means, and a discharge of the second tube means is coupled to the air gap faucet means.

The foregoing and other objects, features, and advantages of the invention will be apparent from the following, more particular, description of the preferred embodiments of the invention, as illustrated in the accompanying drawings.

DESCRIPTION OF THE PREFERRED EMBODIMENTS

Figure 1:
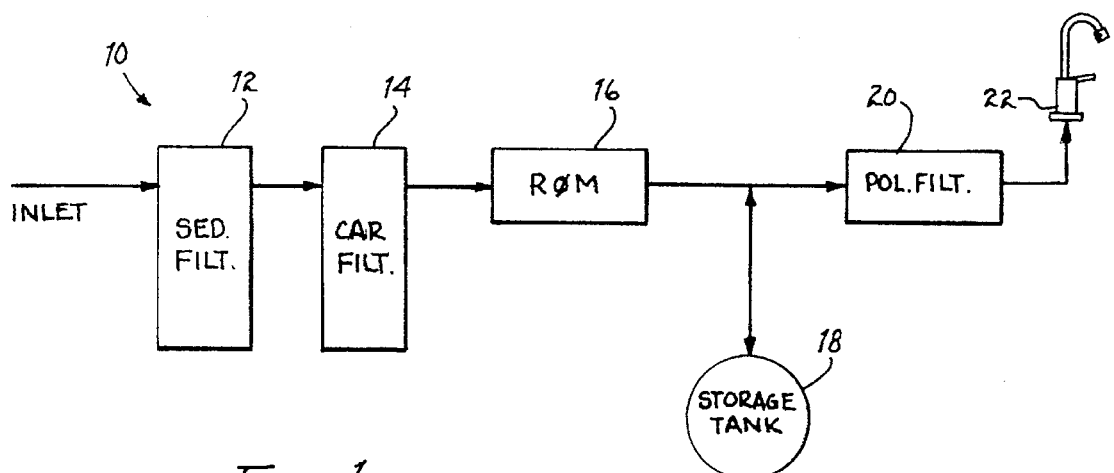
FIG. 1 is a system diagram of a prior art water purification system.

Referring to FIG. 1, a system diagram of a prior art water purification system is shown and generally designated by reference number 10. An inlet supplies water to a sediment filter 12 which removes some particulate matter. The discharge from the sediment filter 12 passes through a carbon filter 14 which removes smaller particulate matter. Most prior art systems 10 remove chlorine ions, which are put in most public water sources for sanitization purposes, in the carbon filter 14. This is significant because any bacteria, viruses, or other microorganisms left in the water after leaving the carbon filter 14 collect and grow in the downstream parts of the system 10. This is the reason most prior art systems 10 require periodic cleansing of the storage tank 18. Water leaving the carbon filter 14 is filtered through a reverse osmosis membrane 16. Water is then either used or stored in the tank 18 for later use. A polishing filter 20 follows the storage tank 18 to remove any undesired taste which may have resulted from contact between the stored water and a rubber bladder found in the storage tank 18. A faucet 22 is used to supply the processed water to a user.

Figure 2:
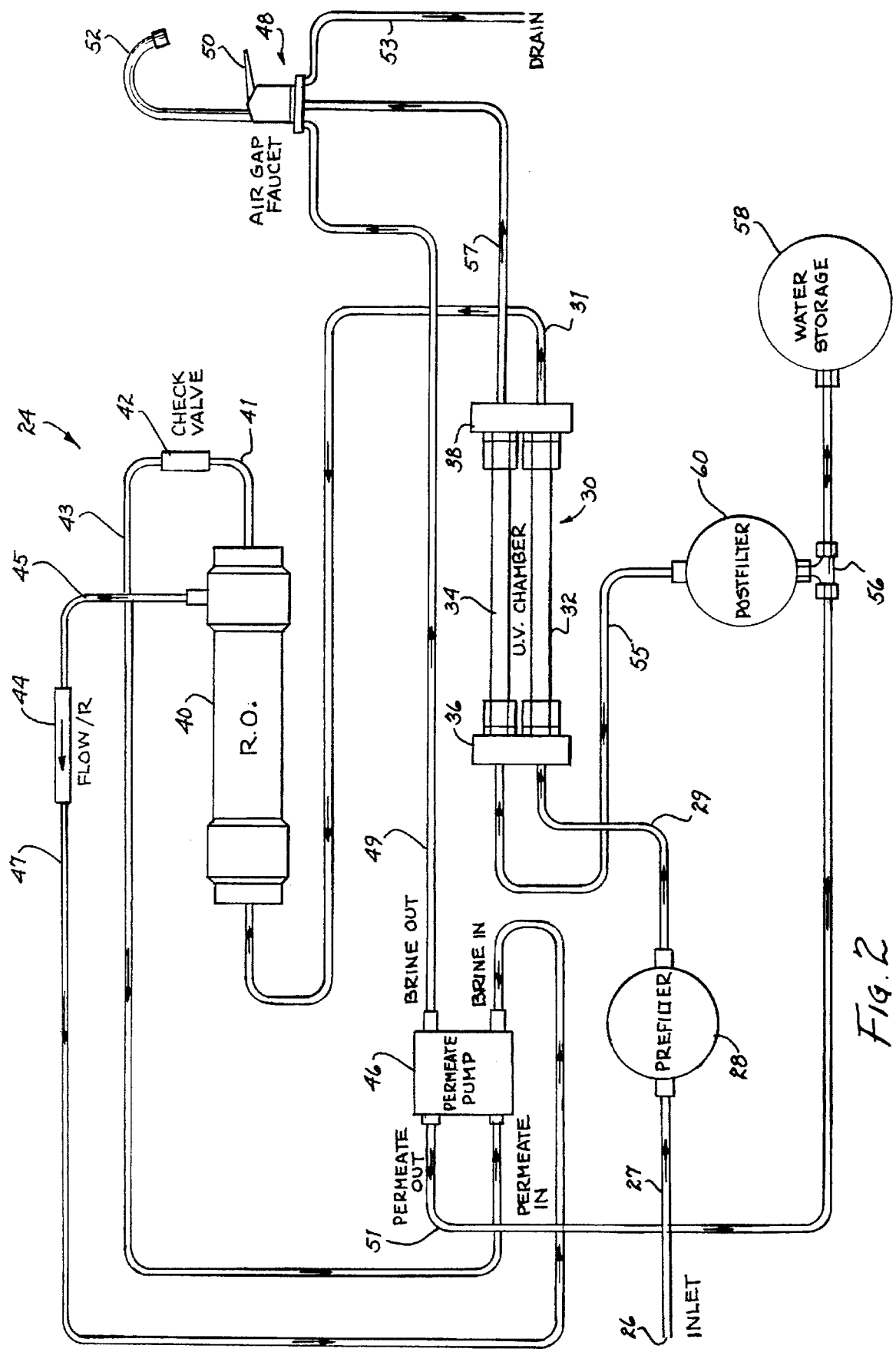
FIG. 2 is a simplified system diagram view of the present invention.

Referring to FIG. 2, a simplified view of the improved water purification system is shown and generally designated by reference number 24. A pressurized source of water is supplied from inlet 26 via tube 27 to a first filter or pre-filter 28. In the preferred embodiment, the pre-filter 28 is a Harmsco #801-1 filter although equivalent filters can be used. Pre-filter 28 removes particulate matter from the water. Tubing 29 carries the discharged water from the pre-filter 28 to the multi-pass ultraviolet chamber 30, or more simply the chamber 30. More specifically, the water enters the first tube 32 of the chamber 30 via a conduit 72 in the support member 36 (see FIG. 3). Note the difference in diameters between the first tube 32 and the conduit 72. The much smaller diameter of the conduit 72 causes the water flowing through the first tube 32 to decelerate, thereby increasing the duration of exposure of the water in the first tube 32 to the ultraviolet light radiation from the ultraviolet light bulb 66 (see FIG. 3). Water exiting the first tube 32 passes through a similar conduit (not shown) in the support member 38 and through tubing 31 to the reverse osmosis chamber 40. The reverse osmosis chamber 40 consists, in a preferred embodiment, of a reverse osmosis housing provided by Flowmatic Systems (part #K-2500N) and an internal membrane provided by NWW Acumem (part #E4001). Equivalent reverse osmosis housings and membranes could be implemented, if desired.

In a manner well known to those skilled in the art, the reverse osmosis chamber 40 provides a first source of water that has not passed through the internal membrane of the reverse osmosis chamber 40. This source of water flows out of the reverse osmosis chamber via tubing 45 and a flow restrictor 44 provided by Payne Manufacturing (part #PFR404M/150). A second source of water passes through the internal membrane of the reverse osmosis chamber 40, the tubing 41, and a check valve 42 provided by Flowmatic Systems (part #C-220-69A). Note that equivalent parts could be used for either the flow restrictor 44 or the check valve 42. The check valve 42 prevents back flow into the reverse osmosis chamber 40 and the flow restrictor 44 slows the rate at which water is allowed into tubing 45, thereby maximizing flow through the internal membrane of the reverse osmosis chamber 40.

The first source of water is conveyed by tubing 47 from the flow restrictor 44 into the BRINE IN line of a permeate pump 46 provided by Aquatic Water Systems (part #ERP1000). Permeate pumps are well known in the art. Other pumps may be used, if desired. The permeate pump 46 uses no electrical power. The flow of the first source of water through the permeate pump 46 from the BRINE IN line to the BRINE OUT line draws the second source of water through tubing 43, the PERMEATE IN line, and the PERMEATE OUT line of the permeate pump 46.

The water flowing out of the BRINE OUT line is conveyed via tubing 49 to an air gap faucet 48. In the preferred embodiment, the air gap faucet 48 is provided by Touch-Flo (part #0-3R03503I) although equivalents thereof may be implemented. Air gap faucets are well known in the art. The "brine" water flow through tubing 49 is discharged from the air gap faucet 48 via line 53 to a drain.

"Good" water from the PERMEATE OUT line of the permeate pump 46 is conveyed via tubing 51 to a header 56 from which the water is directed to either a second filter or post-filter 60 or a water storage tank 58. In the preferred embodiment, the post-filter 60 is provided by Omni (part #OM-0CBC934ROT28) and the water storage tank 58 is provided by P.J.D, International (part #PT-R4); however, equivalents thereof may be used. The water storage tank 58 is provided with an internal bladder (not shown). A pressurized gas such as air is supplied on one side of the bladder so that as water fills the water storage tank 58 on the other side of the bladder, the water in the storage tank 58 is pressurized. Accordingly, water is supplied to the post-filter 60 via both the tubing 51 and the water storage tank 58. If a user is not drawing water from the system 24 and the water storage tank 58 is not filled, water flow from tubing 51 fills the tank 58 until it is full. When the water storage tank 58 is full, the water pressure therein approximately equalizes with the pressure of the water being supplied at the inlet 26, thereby securing water flow into the system 24 until drawn out of equilibrium by a user drawing water from the tank 58. If a user is drawing water from the system 24 and the water storage tank 58 is not full, the user's water is supplied from the tubing 51, and when the user discontinues drawing water, the water flow from tubing 51 again fills the storage tank 58. If a user draws water from the system 24 when the water storage tank 58 is full, the water is supplied from the tank 58, thereby causing pressure in the tank 58 to fall from an equilibrium value and causing system flow to initiate in order to fill the tank 58 again.

Post-filter 60 removes any chlorine that may be in the water as it passes therethrough to tubing 55. Water in tubing 55 enters the second tube 34 of the multi-pass ultraviolet chamber 30 via a conduit 74 in support member 36 (see FIG. 3). As previously explained with respect to the first tube 32, the relatively small diameter of the conduit 74 as compared to the diameter of the second tube 34 causes deceleration of the water flowing therethrough. This enhances the efficiency of the ultraviolet light radiation from the ultraviolet light bulb 66 (see FIG. 3) in killing any viruses, bacteria, or other microorganisms in the water that were not killed in the first pass through the first tube 32. Water exits the second tube 34 via a conduit (not shown) in the member 38 which is similar to conduit 74. The water is then conveyed via tubing 57 to the air gap faucet 48. The air gap faucet 48 has an operating handle 50 for supplying purified water via spigot 52.

Figure 3:
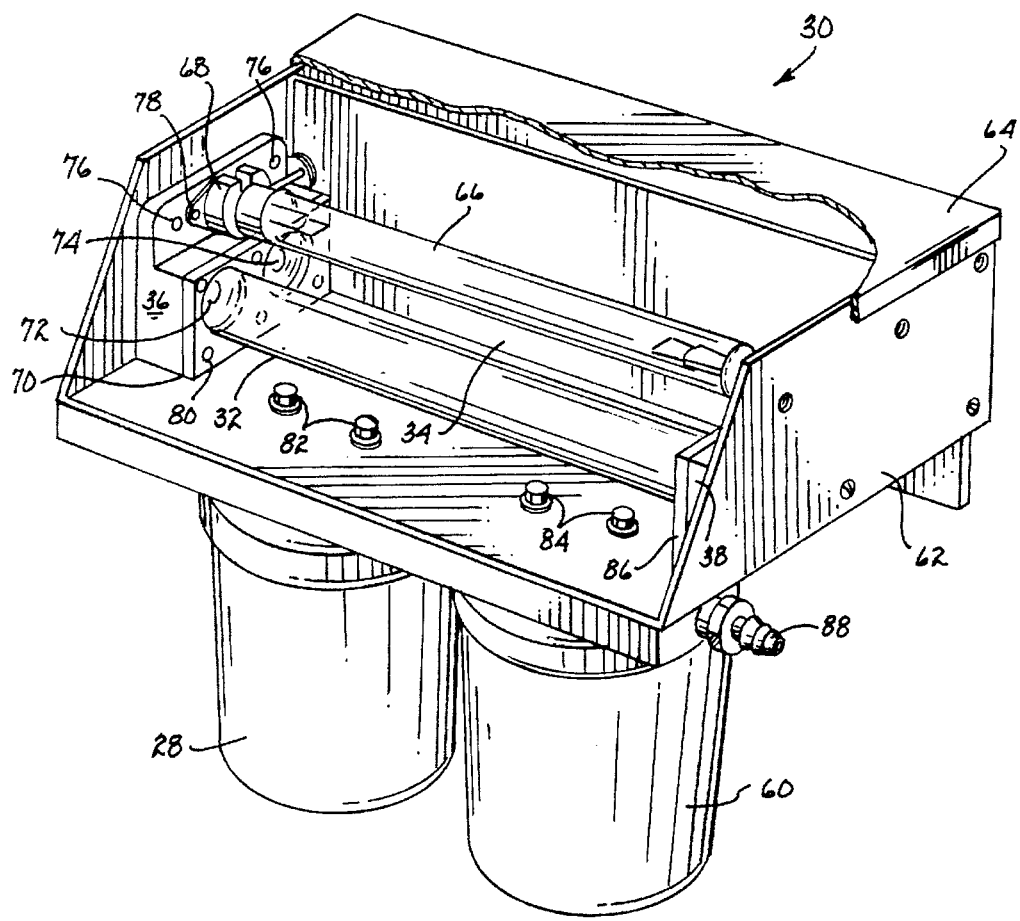
FIG. 3 is a perspective view of the multi-pass ultraviolet chamber of the instant invention. Note that filters are attached on the bottom of the chamber.

Referring to FIG. 3, the multi-pass ultraviolet chamber, or more simply, the chamber 30 is shown with the pre-filter 28 and the post-filter 60 coupled to a bottom side thereof using connectors 82 and 84, respectively. The chamber 30 has a housing 62 with a removable cover 64, thereby permitting easy access to the interior of the chamber 30 for replacing the ultraviolet light bulb 66. Support members 36 and 38 are coupled to opposing inner wall surfaces of the housing 62 using connectors 76. Electrical receptacles 68 are coupled to support members 36 and 38 (only one shown) via connectors 78 for supplying electrical power to the ultraviolet light bulb 66 in a manner well known in the art.

The support members 36 and 38 have cavities (not shown) for receiving an end of each of the tubes 32 and 34. Sealing means such as an O-ring (not shown) circumscribe each end of the tubes 32 and 34 in the vicinity of the cavities into which the tubes are inserted. Securing plates 70 and 86 are coupled to support members 36 and 38, respectively, with connectors 80 for creating a water-tight seal at each junction of the end of the tubes 32 and 34 with their corresponding cavity in the support plates 36 and 38. Again, note that support member 36 has internal conduits 72 and 74 each with a diameter which is significantly smaller than the diameter of the corresponding tube 32 or 34. Thus, water flow into tubes 32 and 34 via conduits 72 and 74, respectively, decelerates because of the expanding volume available for the water flow. This deceleration of water flow through the tubes 32 and 34 increases the exposure time of the water to the ultraviolet light radiation from the ultraviolet light bulb 66, thereby increasing the ability of the system 24 to kill viruses, bacteria, and other microorganisms in the water. Additionally, note that the ultraviolet light bulb 66 is located above and in close proximity to the tubes 32 and 34. This factor also increases system 24 efficiency at killing the aforementioned undesirables in the water. Placing the ultraviolet light bulb 66 above the tubes 32 and 34 also permits easy access to the bulb 66 for replacement once the cover 64 is removed. A nozzle 88 is coupled to the post-filter 60 for connection to tubing 55 (see FIG. 2).

OPERATION

The basic operation of the improved water purification system 24 has been disclosed above; however, a few more advantages of the system 24 follow hereinafter. In particular, the multi-pass ultraviolet radiation capability of the system 24 permits irradiating the water both before and after the water reaches the reverse osmosis chamber 40. Irradiation of the water before entering the reverse osmosis chamber 40 provides the advantage that most if not all of the viruses, bacteria, and other microorganisms are killed before reaching the reverse osmosis chamber 40, thereby eliminating or at least reducing the buildup of these elements inside the reverse osmosis chamber 40. The second pass of the water by the ultraviolet radiation bulb 66 ensures that all viruses, bacteria, and other microorganisms are killed if any have survived the first pass.

Another advantage of this system 24 lies in placing the post-filter 60 downstream of the water storage tank 58 because the chlorine found in most public water supplies is not removed until it passes through the post-filter 60. Accordingly, the water in the storage tank 58 has chlorine which will reduce the number of times that the system 24 would have to be shut down in order to sanitize the water storage tank 58.

Although the invention has been particularly shown and described with reference to a preferred embodiment thereof, it will be understood by those skilled in the art that changes in form and detail may be made therein without departing from the spirit and scope of the invention.

What is claimed is:

1. A water purification system comprising, in combination:

reverse osmosis means for filtering a fluid passing therethrough;

multi-pass ultraviolet chamber means coupled to said reverse osmosis means for irradiating said fluid with ultraviolet light radiation both before and after said fluid passes through said reverse osmosis means;

said multi-pass ultraviolet chamber means comprising:
a housing;
a pair of support members coupled to opposing inner surface wall portions of said housing;
ultraviolet light radiation means coupled between said pair of support members for irradiating said fluid passing through said multi-pass ultraviolet chamber means;
first tube means coupled between said pair of support members for conveying said fluid past said ultraviolet light radiation means prior to said fluid entering said reverse osmosis means;
second tube means coupled between said pair of support members for conveying said fluid past said ultraviolet light radiation means after said fluid has departed from said reverse osmosis means;
each of said support means having conduit means in fluid communication with said first and said second tube means for conveying said fluid therethrough;
diameters of said first and said second tube means being substantially larger than diameters of corresponding conduit means; and
a removable cover located above said ultraviolet light radiation means, said first tube means, and said second tube means.

2. The system of claim 1 further comprising first filter means coupled to an inlet supply of said fluid for filtering said fluid prior to supplying to said first tube means.

3. The system of claim 1 wherein an outlet of said first tube means is coupled to an inlet of said reverse osmosis means.

4. The system of claim 3 wherein said reverse osmosis means provides a first and second output flow of said fluid.

5. The system of claim 4 further comprising permeate pump means driven by said first output flow of said fluid from said reverse osmosis means for pumping said second output flow of said fluid from said reverse osmosis means.

6. The system of claim 5 further comprising air gap faucet means coupled to said first flow from said permeate pump for conveying said first flow to a drain.

7. The system of claim 6 further including air-loaded storage tank means coupled to said second flow from said permeate pump for storing said fluid and for supplying said fluid to a header.

8. The system of claim 7 further including second filter means coupled to said header for filtering said fluid from said permeate pump and from said air-loaded storage tank means.

9. The system of claim 8 wherein a discharge from said second filter means is coupled to an input of said second tube means.

10. The system of claim 9 wherein a discharge of said second tube means is coupled to said air gap faucet means.

11. A water purification system comprising, in combination:

reverse osmosis means for filtering a fluid passing therethrough;

multi-pass ultraviolet chamber means coupled to said reverse osmosis means for irradiating said fluid with ultraviolet light radiation both before and after said fluid passes through said reverse osmosis means;

said multi-pass ultraviolet chamber means comprising:
a housing;

a pair of support members coupled to opposing inner surface wall portions of said housing;

ultraviolet light radiation means coupled between said pair of support members for irradiating said fluid passing through said multi-pass ultraviolet chamber means;

first tube means coupled between said pair of support members for conveying said fluid past said ultraviolet light radiation means prior to said fluid entering said reverse osmosis means;

second tube means coupled between said pair of support members for conveying said fluid past said ultraviolet light radiation means after said fluid has departed from said reverse osmosis means;

each of said support means having conduit means in fluid communication with said first and said second tube means for conveying said fluid therethrough;

diameters of said first and said second tube means being substantially larger than diameters of corresponding conduit means; and a removable cover located above said ultraviolet light radiation means, said first tube means, and said second tube means;

said system further comprising first filter means coupled to an inlet supply of said fluid for filtering said fluid prior to supplying to said first tube means;

wherein an outlet of said first tube means is coupled to an inlet of said reverse osmosis means;

wherein said reverse osmosis means provides a first and second output flow of said fluid;

permeate pump means driven by said first output flow of said fluid from said reverse osmosis means for pumping said second output flow of said fluid from said reverse osmosis means;

air gap faucet means coupled to said first flow from said permeate pump for conveying said first flow to a drain;

air-loaded storage tank means coupled to said second flow from said permeate pump for storing said fluid and for supplying said fluid to a header;

second filter means coupled to said header for filtering said fluid from said permeate pump and from said air-loaded storage tank means;

wherein a discharge from said second filter means is coupled to an input of said second tube means; and wherein a discharge of said second tube means is coupled to said air gap faucet means.

\* \* \* \* \*